United States Patent
Bagaria

(12) 
(10) Patent No.: US 7,067,264 B2
(45) Date of Patent: Jun. 27, 2006

(54) TEST DEVICE FOR DETECTING HUMAN BLOOD AND METHOD OF USE

(76) Inventor: Padma S. Bagaria, P.O. Box 4040, West Hills, CA (US) 91308

( * ) Notice: Subject to any disclaimer, the term of this patent is extended or adjusted under 35 U.S.C. 154(b) by 431 days.

(21) Appl. No.: 09/910,126

(22) Filed: Jul. 23, 2001

(65) Prior Publication Data

US 2003/0027222 A1    Feb. 6, 2003

(51) Int. Cl.
  *G01N 33/567*    (2006.01)
(52) U.S. Cl. .................. 435/7.21; 435/7.92; 435/7.94; 435/287.2; 435/287.7; 435/287.9; 435/805; 435/810; 435/970; 436/63; 436/169; 436/513; 436/514; 436/518; 436/530; 436/805; 436/810
(58) Field of Classification Search ............... 435/7.2, 435/7.92, 7.94, 287.2, 287.7, 287.9, 805, 435/810, 970, 7.1, 7.93; 436/63, 169, 513, 436/514, 518, 530, 805, 810, 501, 515, 523, 436/524, 541, 814
See application file for complete search history.

(56) References Cited

U.S. PATENT DOCUMENTS

| | | | | |
|---|---|---|---|---|
| 4,301,139 A | * | 11/1981 | Feingers et al. | ............ 436/500 |
| 5,415,994 A | * | 5/1995 | Imrich et al. | .................. 435/5 |
| 5,656,503 A | * | 8/1997 | May et al. | .................. 436/514 |
| 5,958,791 A | * | 9/1999 | Roberts et al. | ............. 436/514 |
| 5,998,156 A | * | 12/1999 | Sugiyama et al. | ......... 435/7.92 |
| 6,221,678 B1 | * | 4/2001 | Chandler | .................... 436/530 |
| 6,319,676 B1 | * | 11/2001 | Nazareth et al. | ............. 435/7.5 |
| 6,472,160 B1 | * | 10/2002 | Saruta et al. | ............. 435/7.92 |

FOREIGN PATENT DOCUMENTS

EP    0 291 194    *    4/1988

* cited by examiner

*Primary Examiner*—Bao-Thuy L. Nguyen

(74) *Attorney, Agent, or Firm*—Ted Masters

(57) ABSTRACT

A test device (20) for detecting human blood includes a strip (22) having an introduction station (24), a test station (26), and a control station (28) disposed in spaced apart relationship. The test sample introduction station (24) has labeled antihuman Hb antibodies, the test station (26) has immobilized antihuman Hb antibodies, and the control station has immobilized polyclonal antibodies. A test sample (500) is deposited at the introduction station (24). If human hemoglobin is present in the test sample (500), a colored line will appear at the test station (26) and at the control station (28). If no human hemoglobin is present in the test sample (500), a colored line will only appear at the control station (28).

4 Claims, 5 Drawing Sheets

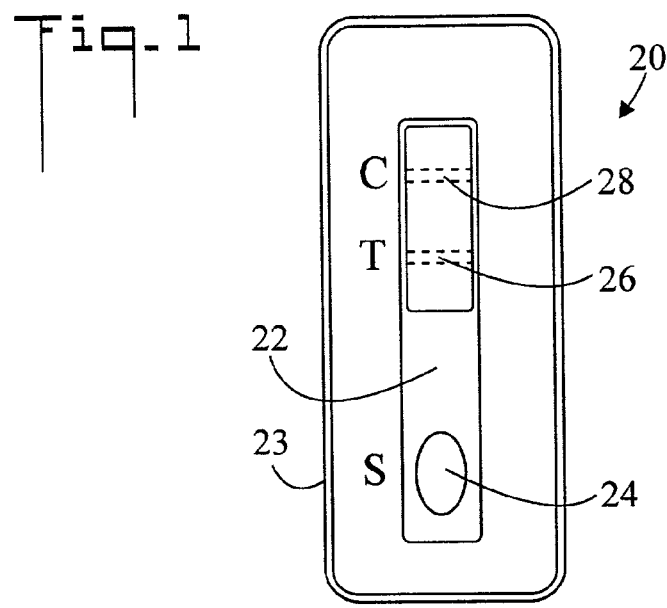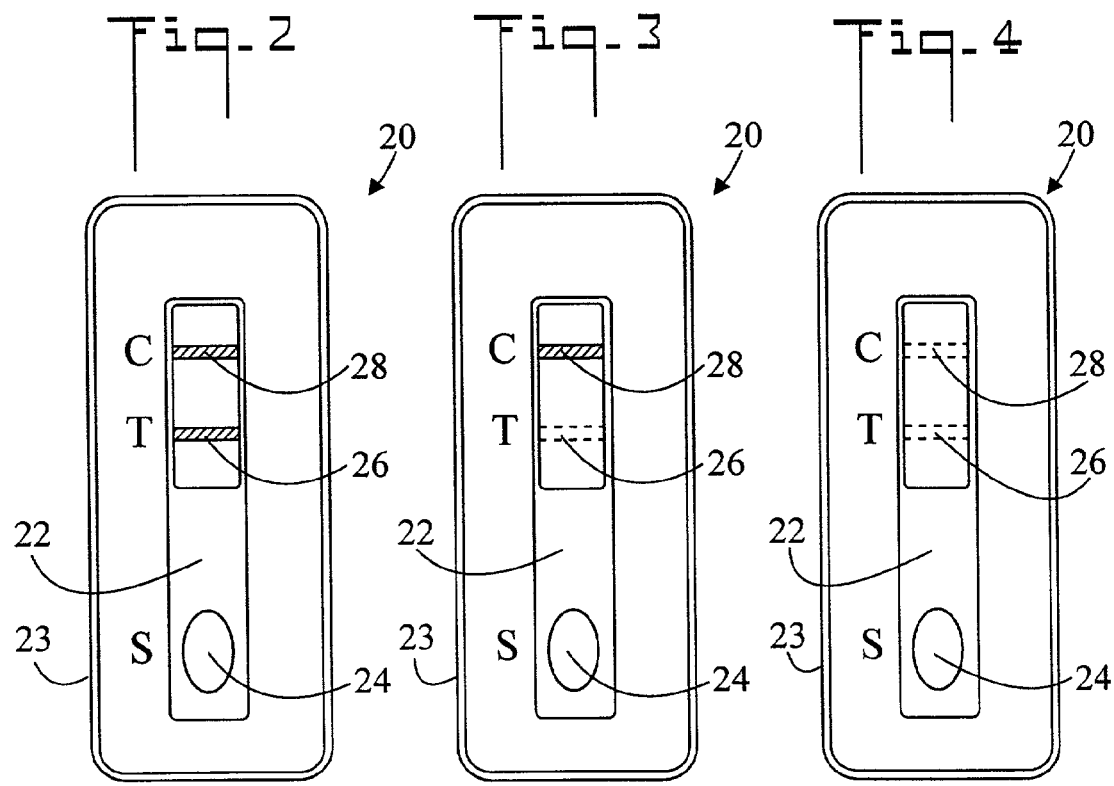

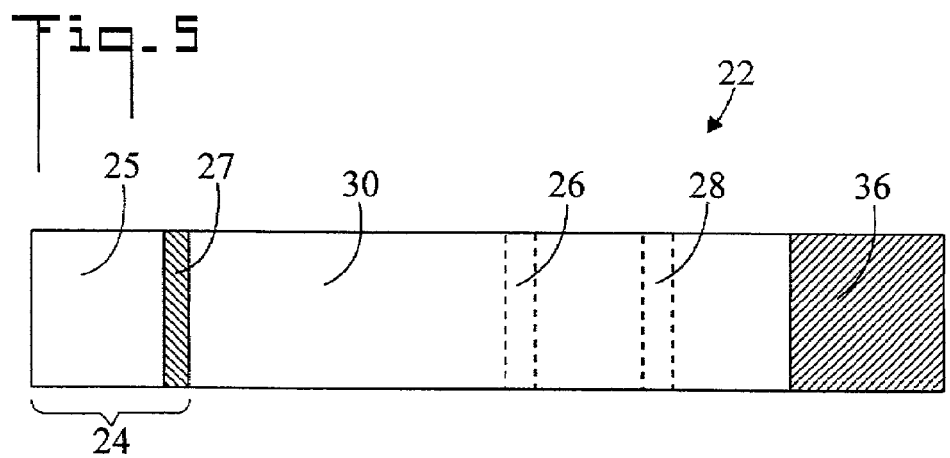
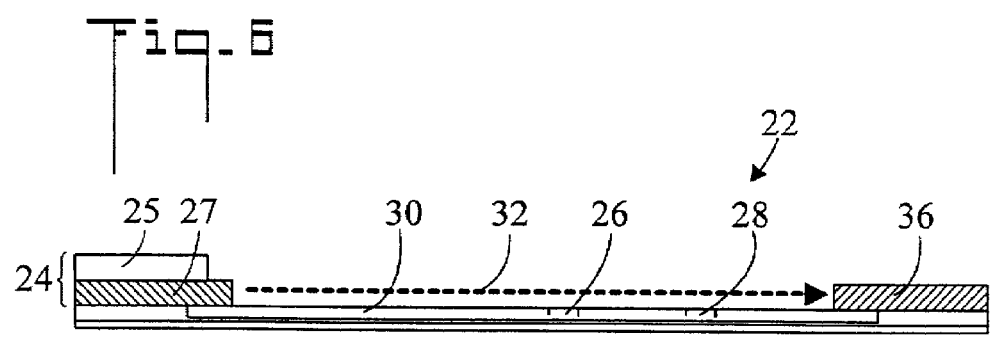

KEY

⅄ MONOCLONAL ANTIHUMAN Hb ANTIBODIES

◯ LABEL

⅄○ LABELED ANTIHUMAN Hb ANTIBODIES

▨ HUMAN HEMOGLOBIN (hHb) ANTIGEN

Y IMMOBILIZED ANTIHUMAN Hb ANTIBODIES

⇧ IMMOBILIZED POLYCLONAL ANTIBODIES

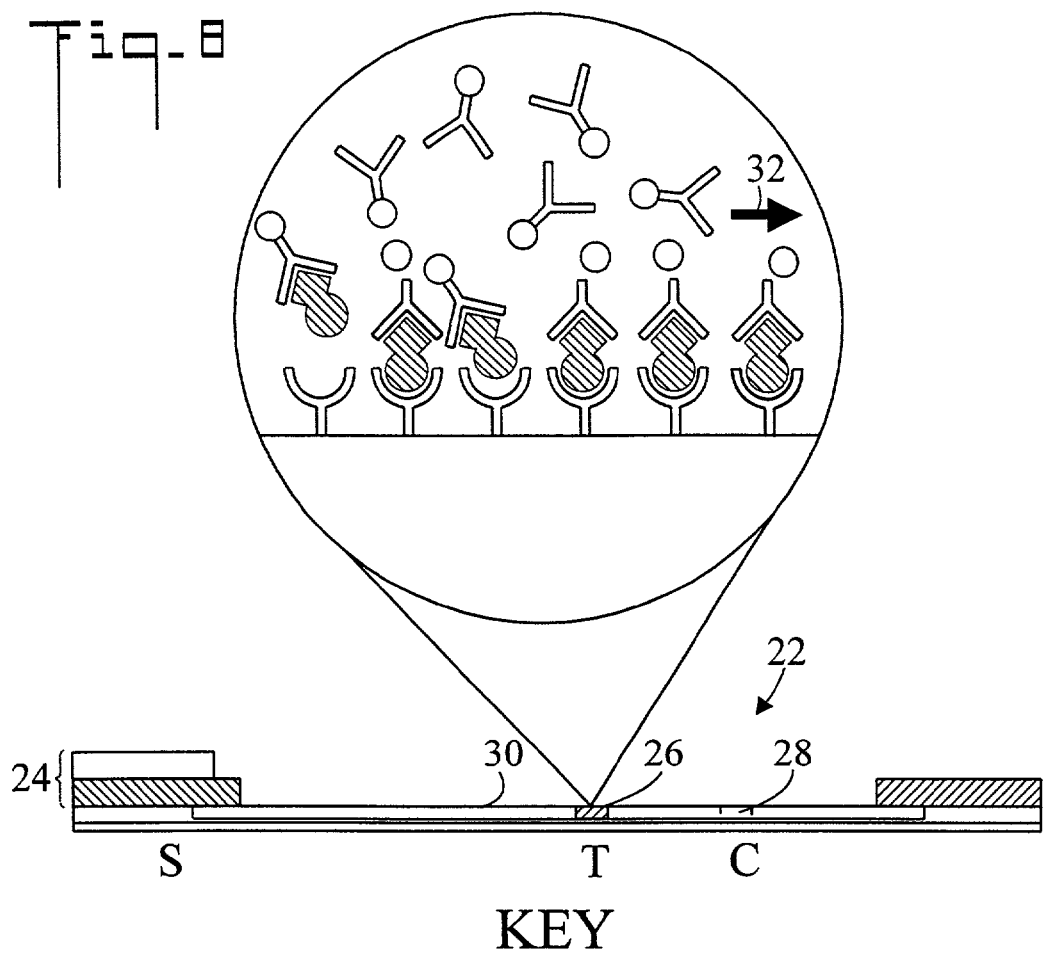

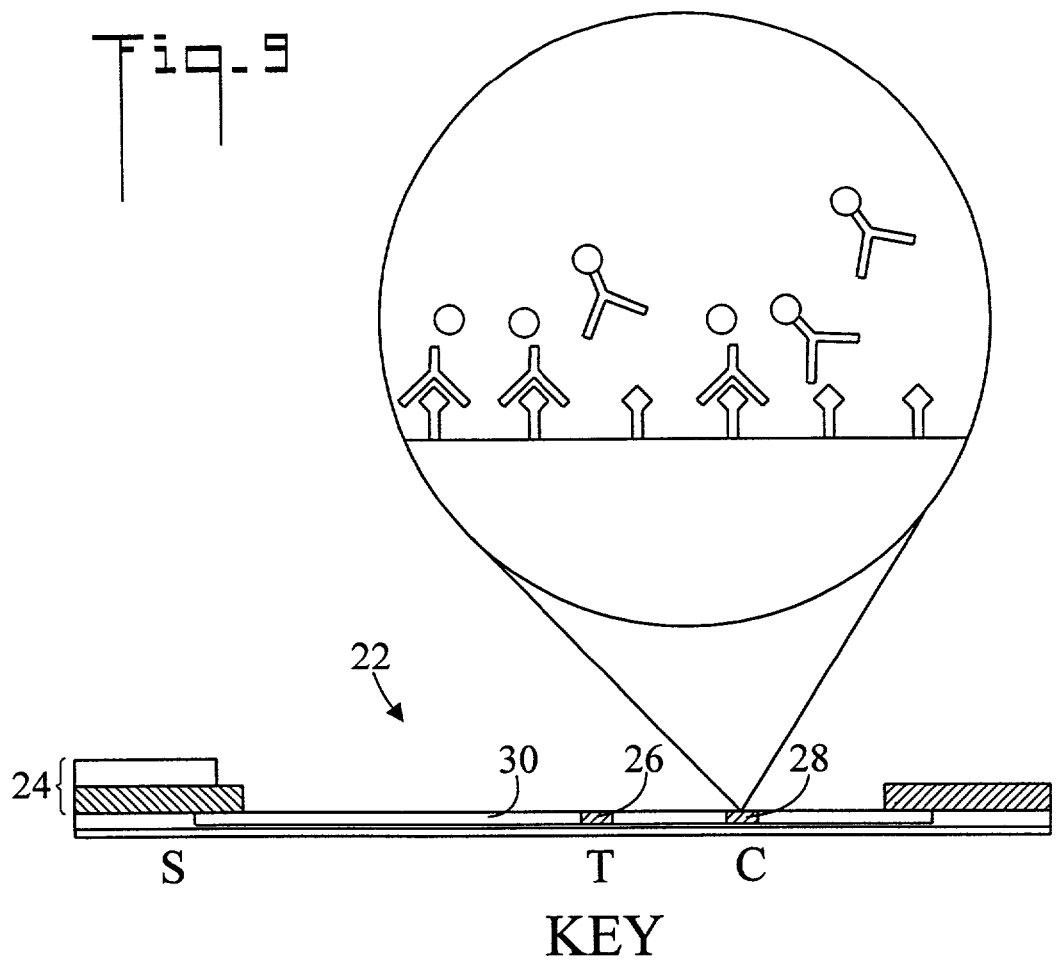
Fig_9
KEY
⅄ MONOCLONAL ANTIHUMAN Hb ANTIBODIES
○ LABEL
⅄ LABELED ANTIHUMAN Hb ANTIBODIES
🜸 HUMAN HEMOGLOBIN (hHb) ANTIGEN
Y IMMOBILIZED ANTIHUMAN Hb ANTIBODIES
⇧ IMMOBILIZED POLYCLONAL ANTIBODIES

TEST DEVICE FOR DETECTING HUMAN BLOOD AND METHOD OF USE

TECHNICAL FIELD

The present invention pertains generally to immunoassays for determining the presence of a particular analyte, and, in particular, to a test device which may be used to detect the presence of human blood.

BACKGROUND ART

Immunoassay test devices are well known in the art. These devices are employed to detect a wide variety of substances. For example, U.S. Pat. No. 4,313,734 shows a method, test kit, and labeled component for the detection and/or determination of one or more components of the reaction between a specific binding protein and the corresponding bindable substance, in which one or more labeled components are used, that are obtained by coupling particles of a dispersion of a metal, metal compound or polymer nuclei, coated with a metal or metal compound, having a particle size of at least 5 nm, directly or indirectly to the desired component of the reaction. During the reaction or after an adequate reaction time, the physical properties and/or the amount of the metal and/or the formed metal containing agglomerate, is/are determined in the test sample, or optionally after a separation of the bound and free metal labeled components in one of the derived fractions.

U.S. Pat. No. 4,376,110 illustrates "two-site" or "sandwich" immunometric assay techniques for determination of the presence and/or concentration of antigenic substances in fluids using monoclonal antibodies. One monoclonal antibody is presented in a soluble labeled form and a second monoclonal antibody is presented bound to a solid carrier; the soluble and bound monoclonal antibodies may be the products of either the same or different cell lines. Each monoclonal antibody has an affinity for the antigenic substances of at least about 108 liters/mole.

U.S. Pat. No. 4,435,504 defines a chromatographic immunoassay employing a specific binding pair member and a label conjugate which delineate a border whose distance from one end of the chromatograph relates to the amount of analyte present. By combining the label conjugate and sample in a solution and immunochromatographing the solution, or employing a combination of enzymes, one enzyme being the label and the other enzyme affixed to the chromatographic support, the position of the border defined by the label can be related to the amount of analyte in the sample solution. Preferably, an immunochromatograph is employed having both a specific binding pair member and an enzyme affixed to the support. A sample is chromatographed and the amount of analyte is determined by (1) contacting the chromatograph with a second enzyme conjugated with a specific binding pair member which binds to the chromatograph in proportion to the amount of analyte bound to the chromatograph, or (2) including the second enzyme conjugate with the sample, resulting in a defined border related to the amount of analyte in the sample. The two enzymes are related in that the substrate of one is the product of the other, so that upon contact of the chromatograph with appropriate reagents, a detectable signal develops which permits detection of the border to which the analyte traveled. This distance can be related to the amount of analyte present in the sample.

U.S. Pat. No. 4,703,017 concerns a solid phase assay for an analyte where the binder is supported on a solid support, such as nitrocellulose, and the tracer is comprised of ligand labeled with a colored particulate label, such as a liposome including a dye. The assay has a high sensitivity, and the tracer is visible on the support under assay conditions without instrumentation and without further treatment.

U.S. Pat. No. 4,855,240 consists of a test device and assay for determining an analyte where the tracer and sample may be simultaneously applied to different absorbent material portions both in capillary flow communication with an absorbent material portion having a binder. The sample contacts the binder prior to any substantial contact between the sample and tracer or the tracer and binder.

U.S. Pat. No. 4,954,452 describes a method of performing a diagnostic immunoassay utilizing colloidal non-metal particles having conjugated to them a binding component capable of specifically recognizing an analyte to be determined. After reaction of the sample and colloidal non-metal particles, the presence or amount of analyte/colloidal non-metal particle complexes is determined by optical analysis as a measure of the amount of analyte in the sample. The method can be utilized for the specific detection of numerous analytes and is sensitive and has a wide detection range.

U.S. Pat. No. 5,028,535 is directed to a ligand-receptor assay for determining the presence or amount of at least one target ligand capable of competing with a ligand analogue conjugate for binding sites available on a ligand receptor. The ligand analogue conjugate has at least one ligand analogue coupled to a signal development element capable of emitting a detectable signal, in a fluid sample suspected of containing the target ligand. The assay includes the steps of: a. contacting the fluid sample with the ligand analogue conjugate and ligand receptor to form a reaction mixture, the relative amounts of ligand analogue conjugate and ligand receptor being such that in the absence of the target ligand, and subsequent to substantially equilibrium binding, substantially all of the ligand analogue conjugate is bound to the ligand receptor; b. detecting the unbound ligand analogue conjugate; and, c. relating the detectable signal to the presence or amount of target ligand in the fluid sample. In one embodiment an optional means also is employed for removing the receptor from the reaction mixture. In other assay formats, the analyte of interest may be either a ligand receptor or ligand.

U.S. Pat. No. 5,075,078 shows an improved chromatographic strip binding assay device for determining the presence or amount of an analyte present in a patient sample. Assay label reagents interact with capture reagents immobilized in a testing region on the strip substrate to generate a visually detectable image indicative of the test result. The test result images include a minus sign (−) to indicate a negative test result if the suspect analyte is absent in the patient sample and a plus sign (+) to indicate a positive test result if the suspect analyte is present or is present at a pre-determined concentration in the patient sample. The immobilized capture reagents responsible for the location and configuration of the test result images are applied to the strip at an angled orientation with respect to the fluid flow direction of the strip to ensure that sharp, substantially complete test result images are formed during performance of the assay. The devices are designed to provide substantially self-performing assays having inherently clear test results which are not subject to misinterpretation by the skilled or untrained user.

PCT Application WO 95/16207 is directed to an assay device with a barrier for regulating reagent application. An assay device for detection and/or determination of an analyte in a test sample uses a barrier containing an aperture to control the application of reagents to the device for greater reproducibility of results.

U.K. Patent 2,204,398 pertains to an analytical test device for use in assays. The device is suitable for use in the home, clinic, or doctor's surgery, and is intended to give an analytical result which is rapid and which requires the minimum degree of skill and involvement from the user. In a typical embodiment, the test device comprises a hollow casing containing a dry porous carrier which communicates directly or indirectly with the exterior of the casing such that a liquid test sample can be applied to the porous carrier.

The conventional test methods for blood detection have several disadvantages: they are not sensitive enough, they are not specific, they are cumbersome, and they require procedures that are time consuming to perform in forensic laboratories.

DISCLOSURE OF INVENTION

The present invention is directed to a test device of the immunoassay variety which detects the presence of human (or primate) hemoglobin in blood. The test device of the present invention overcomes the disadvantages of prior art blood tests by providing accurate results that are easy to interpret and can be performed and results made available in about ten minutes or less. The test device can be used at crime scenes, in forensic laboratories, and at field sites.

A 150 μl sample is added to the test sample introduction station. If human hemoglobin (hHb) antigen is present in the specimen, it will react with a mobile labeled monoclonal antihuman Hb antibody present in the test sample introduction station forming a mobile labeled antibody-antigen complex. This mobile labeled antibody-antigen complex migrates through an absorbent membrane towards a test station. An immobolized polyclonal antihuman Hb antibody is present at the test station. This immobilized antibody captures the above complex so that an antibody-antigen-antibody sandwich is formed releasing the labels in a narrow zone on the membrane. When the Hb concentration in the sample exceeds 0.05 μg/ml, the labels, which are preferably pink, will form a pink colored band in the test station. If no hHb is present, a pink band in the test station will not result. Labeled monoclonal Hb antibodies that do not bind with the Hb antibody migrate along the membrane to a control station having an immobilized polyclonal antibody where they are captured forming a complex releasing the labels. A pink band will then form in the control station. The presence of two pink lines, one in the test area and other in the control station indicates a positive result, while a line only in the control station indicates a negative result.

In accordance with a preferred embodiment of the invention, the test device for detecting human (or primate) hemoglobin comprises a strip having a test sample introduction station, a test station, and a control station, the stations being disposed in spaced apart relationship along the strip. In a ready for use test device, the test sample introduction station includes labeled antihuman Hb antibodies, the test station includes immobilized antihuman Hb antibodies, and the control station includes immobilized polyclonal antibodies.

In accordance with another preferred embodiment, the test sample introduction station includes labeled monoclonal antihuman Hb antibodies, and the test station includes immobilized polyclonal antihuman Hb antibodies or monoclonal antihuman Hb antibodies.

In accordance with another preferred embodiment, the test station also includes immobilized human IgM antibodies with immobilized monoclonal antibodies antihuman Hb being preferred.

In accordance with a important aspect of the invention, the labeled antihuman Hb antibodies have a label selected from the group consisting of colloidal gold, colloidal silver, carbon, latex, dye, and enzyme.

Other features and advantages of the present invention will become apparent from the following detailed description, taken in conjunction with the accompanying drawings, which illustrate, by way of example, the principles of the invention.

BRIEF DESCRIPTION OF DRAWINGS

FIG. 1 is a top plan view of the test device prior to use;

FIG. 2 is a top plan view of the test device after use showing the presence of human hemoglobin;

FIG. 3 is a top plan view of the test device after use showing no human hemoglobin present;

FIG. 4 is a top plan view of the test device after use showing an invalid test;

FIG. 5 is a top plan view of a test strip portion of the test device for detecting human hemoglobin in accordance with the present invention;

FIG. 6 is a side elevation view of the test strip;

FIG. 8 is a side elevation view of the test strip showing the substances present at the test station after the introduction of a liquid test sample containing human hemoglobin; and, FIG. 9 is a side elevation view of the test strip showing the substances present at the control station after the introduction of a liquid test sample.

MODES FOR CARRYING OUT THE INVENTION

Figure 7:
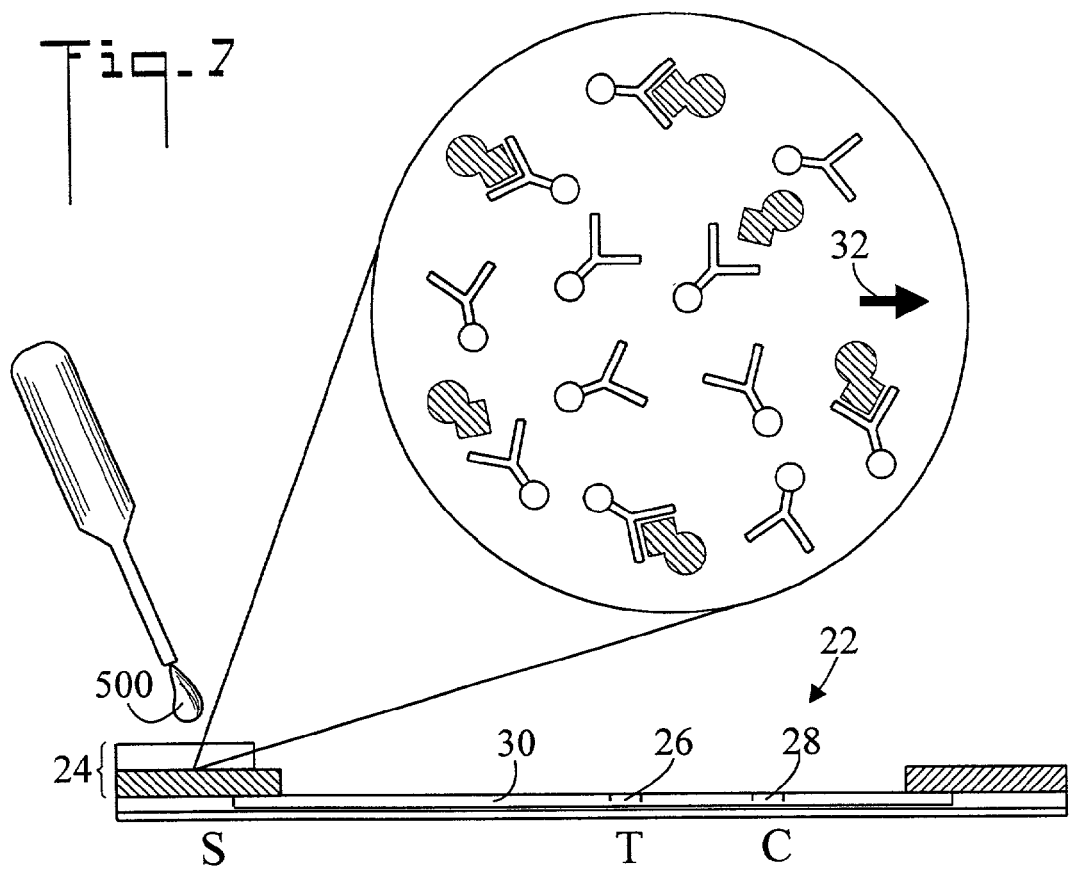
FIG. 7 is a side elevation view of the test strip showing the substances present at a test sample introduction station after the introduction of a liquid test sample containing human hemoglobin.

Referring initially to FIG. 1, there is illustrated a test device for detecting human hemoglobin in blood in accordance with the present invention, generally designated as 20. Test device 20 includes a strip 22 (also refer to FIGS. 5 and 6) having a test sample introduction station 24 ("S"), a test station 26 ("T"), and a control station 28 ("C"), the stations being disposed in spaced apart relationship. Strip 22 is disposed within a housing 23 having apertures for introducing a test sample and viewing the test results. In the figure, test station 26 and control station 28 are shown in dashed lines indicating their location on strip 22. Prior to the test, the stations are the same color as the membrane member 30 (FIGS. 5 and 6) which is usually white and are therefore not visually discernible prior to the test. A liquid test sample is introduced at test sample introduction station 24 which migrates in all directions including along strip 22 first to test station 26 and then to control station 28.

FIG. 2 is a top plan view of test device 20 after use showing the presence of human hemoglobin. If human (or primate) hemoglobin is present in the test sample, a colored line indicated by a hashed area has appeared at both test station 26 and control station 28.

FIG. 3 is a top plan view of test device 20 after use showing no human hemoglobin present. If there is no human hemoglobin present in the test sample, no colored line appears at test station 26, but a colored line does appear at control station 28.

FIG. 4 is a top plan view of test device 20 after use showing an invalid test. The fact that no colored line appears at control station 28 dictates that the test was inconclusive and should be repeated using another test device 20.

FIGS. 5 and 6 are illustrate top plan and side elevation views, respectively, of the strip 22 portion of test device 20. In a preferred embodiment, test sample introduction station 24 includes a sample pad 25 and a conjugate pad 27. Sample pad 25 is disposed above conjugate pad 27, distributes the test sample 500 (FIG. 7) over the conjugate pad 27, removes particles from the test sample 500, can adjust the pH or viscosity of the test sample 500, and facilitates the release of the detector reagent. Strip 22 comprises an elongated membrane member 30 which both absorbs and promotes migration of a sample 500. In a preferred embodiment, membrane member 30 is made of nitrocellulose and is usually white. Test sample 500 is introduced at test sample introduction station 24 (sample pad and conjugate pad), and migrates along membrane member 30, first to test station 26, then to control station 28, and lastly to an absorbent pad 36. On strip 22, test introduction station 24, test station 26, and control station 28 are disposed in spaced apart relationship.

FIG. 7 illustrates a side elevation view of strip 22 showing the substances present at test sample introduction station 24 after the introduction of a liquid test sample 500 containing human hemoglobin having the human hemoglobin Hb antigen. In usual practice, a test sample 500 is diluted with distilled water, or buffers such as TRIS or PBS. At the test sample introduction station 24, mobile labeled antihuman Hb antibodies are present on the conjugate pad 27 having the label loosely bonded to the antihuman Hb antibody forming a conjugate. In a preferred embodiment, the labeled antihuman Hb antibodies are labeled monoclonal antihuman Hb antibodies. The label, which provides a visual indication of a positive result, is selected from the group consisting of colloidal gold, colloidal silver, carbon, latex, dye, and enzyme. When a test sample 500 containing the human hemoglobin Hb antigen is deposited, some of the human hemoglobin Hb antigen binds to the labeled antihuman Hb conjugate forming a complex, while other labeled antihuman Hb conjugate remains unbound. Both the bound and unbound labeled antihuman Hb antibodies migrate in direction 32 along membrane member 30 toward test station 26.

FIG. 8 is a side elevation view of strip 22 showing the substances present at test station 26 after the mixture has reached the test station. Test station 26 has immobilized antihuman Hb antibodies. In a preferred embodiment, the immobilized antihuman Hb antibodies are immobilized polyclonal antihuman Hb antibodies. In another preferred embodiment, immobilized human IgM antibodies (immobilized monoclonal human IgM antibodies being preferred) are also present at test station 26. The combination of immobilized antihuman Hb antibodies and immobilized monoclonal human IgM antibodies may result in better blocking and more specific test results. At the test station 26, the labeled antibody-antigen complexes arriving from the test sample introduction station 24 bind with the immobilized antihuman Hb antibodies to form a sandwich. In the process, the label is released providing a visual indication, in the form of a colored line, that the human hemoglobin Hb antigen is present in the test sample 500. The unbound labeled monoclonal antihuman Hb antibodies continue to migrate along membrane 30 in direction 32 toward control station 28.

FIG. 9 is a side elevation view of strip 22 showing the substances present at control station 28 when the mixture reaches the control station. Control station 28 has immobilized polyclonal antibodies. Labeled antihuman Hb antibodies arriving at control station 28 from test station 26 bind with the immobilized polyclonal antibodies releasing the label and providing a colored line. The colored line is created whether the orginal test sample 500 did or did not contain the human hemoglobin Hb antigen. It serves merely to show that enough sample was deposited to wet the entire strip 27 including the area of control station 28.

In a preferred embodiment the follow concentrations have been found useful for a test device 20: at the test sample introduction station 24, 2 micrograms of labeled monoclonal antihuman Hb antibodies; at the test station 26, 5 micrograms of immobilized antihuman Hb antibodies and 2 micrograms of immobilized human IgM antibodies; and, at the control station 28, five micrograms of immobilized polyclonal antibodies. Additionally, in a preferred embodiment, a protein stabilizer such as bovine serum albumin has been found to be useful in an amount of 1 microgram per test device 20. Also, a preservative such as sodium azide is used in an amount of 0.1 microgram per test device 20 for enhancing shelf life. And, two buffers have been found to be useful: sodium dibasic phosphate in an amount of 0.025 micrograms per test device 20, and sodium chloride in an amount of 0.085 micrograms per test device 20.

One method for determining the presence of human hemoglobin, using the present invention includes the following steps:

a. providing a test device 20 including a strip 22 having a test sample introduction station 24, a test station 26, and a control station 28 with the stations disposed in a spaced apart relationship with the test sample introduction station 24 having labeled antihuman Hb antibodies, the test station 26 having immobilized antihuman Hb antibodies, and the control station 28 having immobilized polyclonal antibodies;

b. depositing a test sample 500 containing human hemoglobin Hb antigen at the test sample introduction station 24;

c. allowing the human hemoblobin Hb antigen to bind with some of the labeled antihuman Hb antibodies to form a complex, both the complex and unbound labeled antihuman Hb antibodies to migrate to the test station 26, at the test station 26 the complex to bind with the immobilized antihuman Hb antibodies releasing the labels thereby providing a visual indication, the unbound labeled antihuman Hb antibodies to migrate to the control station 28, and, at the control station the unbound labeled antihuman Hb antibodies to bind with the immobilized polyclonal antibodies releasing the labels thereby providing a visual indication; and, d. observing the visual indications at the test and control stations.

The method may also be used for determining a lack of presence of human hemoglobin including the following steps:

a. providing a test device 20 which includes a strip 22 having a test sample introduction station 24, a test station 26, and a control station 28 with the stations disposed in a spaced apart relationship, the test sample introduction station 24 having labeled antihuman Hb antibodies, the test station 26 having immobilized antihuman Hb antibodies, and the control station 28 having immobilized polyclonal antibodies;

b. depositing a test sample 500 containing no human hemoglobin Hb antigen at the test sample introduction station 24;

c. allowing unbound labeled antihuman Hb antibodies to migrate to the test station 26, at the test station 26 no reaction taking place and no visual indication being present, the unbound labeled antihuman Hb antibodies to migrate to the control station 28, and, at the control station 28 the unbound labeled antihuman Hb antibodies binding with the immobilized polyclonal antibodies releasing the labels thereby providing a visual indication; and, d. observing the lack of a visual indication at the test station and the presence of a visual indication at the control station.

Test Protocol

The test device is sealed in a test pouch with a desiccant to prolong shelf life. An extraction tube containing extraction buffer is provided with each device. A clock or timer is needed for timing the test and a centrifuge can be used to concentrate the sample. Samples may be obtained from blood-stained fibers from clothing, small blood particles scraped off a stain, fibers from a moist cotton swab used to collect stains, and liquid blood. If the specimen is fresh, either a slide or the extraction tube may be used. The specimen is soaked for at least 1–5 minutes in the entire volume of buffer in the extraction tube and may then be immediately used. If the specimen is not fresh, useful results may still be obtained from blood stains that have been subjected to room temperatures for up to five years. Extraction of specimens from aged blood-stained materials may be performed either on a slide or in the extraction tube. The specimen is soaked for at least 30 minutes in the entire volume of buffer in the extraction tube. The aged blood stain may also be soaked in 2–3 drops of 5% ammonia for 2–5 minutes to extract the hemoglobin until the ammonia evaporates. The 2–3 drops of extraction buffer are added. The pH of the sample must be between 1 and 9. The sample may then be immediately used. If the sample is also to be used for a DNA assay, the stain is soaked in 600 µl of HEPES buffer with the length of the soak depending on the age of the stain. After a pH between 1 and 9 is determined, the sample is centrifuged for 3 minutes. A 150 µL sample of the resulting supernatant is used for the test of the present method and the remaining sample is available for DNA analysis. Luminol reagents may also be used in the above procedure.

After the sample has been prepared and has warmed to room temperature, four drops or 150 µL of sample are deposited in the sample introduction station 24 of the test device. The result is read at 10 minutes. A positive result can be seen as early as after 2 minutes depending upon the hHb concentration but confirmation of a negative result requires the full 10 minutes. The result should not be read after 10 minutes because nonspecific reactions may occur and may result in false positives. If two pink lines are present, one each in the test station 26 and the control station 28, the test result is positive and indicates that human hemoglobin is present at a level at or above 0.05 µg/ml. If there is only one pink line in the control station 28, the test result is negative indicating no human hemoglobin is present at a level at or above 0.05 µg/ml or the presence of a high dose hook effect.

A high dose hook effect occurs when the human Hb concentration is too high since the test device is very sensitive. When abundant human Hb is available, some binds to the labeled antibody to form the labeled antibody—antigen complex and some is free to migrate toward the test station 26. The immobilized antibody in the test station 26 is blocked by this free Hb. The mobile labeled antibody—antigen complex which ordinarily provides the pink color cannot bind to the antibody. As a result, no pink line will form in the test station 26 although a lot of Hb is present in the sample giving a false negative result. If a high dose hook effect is suspected, the sample may be retested using a 1 to 100 dilution.

Specificity.

The test device is specific for human hemoglobin subtypes $HbA_0$, $HbA_2$, HbF, HbS and for hemoglobin derived from primates (anthropoideae). No cross reactivity to hemoglobin from amphibians, birds, beef, fish, goat, horse, mammals, rabbit, sheep, turkey has been observed up to 1000 µg/ml each. No cross reactivity to horse radish peroxidase has been observed up to 2000 µg/ml. No prozone effect was detected up to a hemoglobin concentration of 2000 µg/ml in the transport medium.

The preferred embodiments of the invention described herein are exemplary and numerous modifications, dimensional variations, and rearrangements can be readily envisioned to achieve an equivalent result, all of which are intended to be embraced within the scope of the appended claims.

I claim:

1. A method for determining the presence of human blood, comprising:

providing a test device including a strip having a test sample introduction station, a test station, and a control station, said stations disposed in spaced apart relationship, said test sample introduction station including labeled antihuman Hb antibodies, said test station including immobilized antihuman Hb antibodies and immobilized human IgM antibodies, and said control station including immobilized polyclonal antibodies;

depositing a test sample suspected of containing human hemoglobin Hb antigen at said test sample introduction station;

allowing said human hemoglobin Hb antigen to bind with some of said labeled antihuman Hb antibodies to form a complex, both said complex and unbound labeled antihuman Hb antibodies to migrate to said test station, at said test station said complex to bind with said immobilized antihuman Hb antibodies thereby providing a visual indication, said unbound labeled antihuman Hb antibodies to migrate to said control station, and, at said control station said unbound labeled antihuman Hb antibodies to bind with said immobilized polyclonal antibodies thereby providing a visual indication; and, observing said visual indications at both said test station and said control station, thereby confirming the presence of human blood.

2. The method according to claim 1, further including: taking about 10 minutes or less to perform said method.

3. A method for determining a lack of presence of human blood, comprising:

providing a test device including a strip having a test sample introduction station, a test station, and a control station, said stations disposed in spaced apart relationship, said test sample introduction station including labeled antihuman Hb antibodies, said test station including immobilized antihuman Hb antibodies and immobilized human IgM antibodies, and said control station including immobilized polyclonal antibodies;

depositing a test sample suspected of containing no human hemoglobin Hb antigen at said test sample introduction station;

allowing unbound labeled antihuman Hb antibodies to migrate to said test station, at said test station no reaction taking place, said unbound labeled antihuman Hb antibodies to migrate to said control station, at said control station said unbound labeled antihuman Hb antibodies to bind with said immobilized polyclonal antibodies thereby providing a visual indication; and, observing no visual indication at said test station, and observing said visual indication at said control station, thereby confirming a lack of presence of human blood.

4. The method according to claim 3, further including: taking about 10 minutes or less to perform said method.

* * * * *